(12) United States Patent
Burrows

(10) Patent No.: US 7,906,157 B2
(45) Date of Patent: Mar. 15, 2011

(54) **USE OF EXTRACTS OF *CAPRARIA BIFLORA* IN THE PREVENTION AND/OR TREATMENT OF SENILE CATARACTS**

(75) Inventor: Adria Burrows, New York, NY (US)

(73) Assignee: Burrows Enterprises, LLC, New York, NY (US)

( * ) Notice: Subject to any disclaimer, the term of this patent is extended or adjusted under 35 U.S.C. 154(b) by 28 days.

(21) Appl. No.: 12/432,114

(22) Filed: Apr. 29, 2009

(65) Prior Publication Data

US 2009/0280204 A1 Nov. 12, 2009

Related U.S. Application Data

(60) Provisional application No. 61/051,080, filed on May 7, 2008.

(51) Int. Cl.
*A01N 65/00* (2009.01)
(52) U.S. Cl. ........................................... 424/725
(58) Field of Classification Search .................. None
See application file for complete search history.

(56) References Cited

OTHER PUBLICATIONS

Acosta, S.L. et al., Analgesic properties of *Capraria biflora* leaves aqueous extract, Fitoterapia, 2003, pp. 686-688, vol. 74, Elsevier.
Acosta, S.L. et al., Anti-inflammatory Effects of an Aqueous Extract of *Capraria bifloral* L., Acta Farm. Bonaerense, 2003, vol. 22, No. 1. pp. 53-55.
Longuefosse, Louis-Jean et al., Medical ethnobotany survey in Martinique, Journal of Ethnopharmacology, 1996, pp. 117-142, vol. 53, Elsevier.

*Primary Examiner* — Michael V Meller
(74) *Attorney, Agent, or Firm* — Gottlieb, Rackman & Reisman, P.C.

(57) ABSTRACT

The invention provides methods for treating and/or preventing the recurrence of a senile cataract, and/or for inhibiting the development of a senile cataract and/or an incipient senile cataract, in a human or animal subject. The invention further provides nutraceutical compositions suited for the same, derived from an extract of the plant *Capraria biflora*. The compositions comprise the extract in a therapeutically sufficient amount for the treatment and/or prophylaxis of a senile cataract in a human and/or animal subject.

16 Claims, No Drawings

USE OF EXTRACTS OF *CAPRARIA BIFLORA* IN THE PREVENTION AND/OR TREATMENT OF SENILE CATARACTS

REFERENCE TO RELATED APPLICATIONS

This application claims the benefit of prior U.S. Provisional Patent Application Ser. No. 61/051,080, filed May 7, 2008.

TECHNICAL FIELD

The present invention relates broadly to the field of healthcare, and in particular, to the field of ophthalmology, which involves the care of the eyes and vision. More specifically, this invention relates to novel non-surgical methods, having both medical and veterinary application, for the prevention and/or treatment of a particular class of cataracts; the invention also relates to herbal formulations that find use in such methods, and which were previously unknown for such use.

BACKGROUND OF THE INVENTION

A cataract is a condition in which an opacity develops in the crystalline lens of an eye or in the ocular envelope; the opacity may range from only slight to complete obstruction of the passage of light. The development of a cataract may lead initially to near-sightedness (myopia) in the affected eye (or eyes), and may progress to blindness if left untreated. Moreover, untreated cataracts can cause severe inflammation and/or glaucoma, and may even cause dislocation of the lens.

Senile cataracts are an age-related phenomenon, occurring most commonly in human subjects who are fifty years of age and older, but age-related cataracts also occur in the later lives of other animals, including species in other Families of Order Primates, as well as species from other Orders and Families of Class Mammalia, such as mice and rats (Order Rodentia), dogs (Family Carnidae), cats (Family Felidae), horses (Family Equidae), cows (Family Bovidae) and other higher mammals. Species from other non-mammalian Classes, such as birds (Class Aves), are also affected by senile cataracts.

Presently, cataract surgery is the only generally accepted treatment for cataracts (senile or otherwise), and for reasons that are self-evident, is performed almost exclusively only in humans. In cataract surgery, the affected lens is removed (excised) and replaced by a synthetic (generally plastic or silicone) intraocular lens. While this procedure typically provides human patients with at least 20/40 vision, it is not without its drawbacks.

After surgery, the patient's mobility is reduced and his/her activity level must be somewhat suppressed for some time. Moreover, after cataract extraction surgery, some patients require an additional procedure to remove cloudiness that may develop within the posterior capsule. Glaucoma, retinal detachment, endophthalmitis and bacterial infection are all possible complications that may result from, and follow upon, cataract extraction surgery. Furthermore, some human patients may not be candidates for cataract extraction surgery, due to either a pre-existing medical condition or an unwillingness to undergo an ocular surgery, and animals suffering from senile cataracts are rarely candidates for cataract extraction surgery, since unlike human subjects, in most cases the extracted lens would not be replaced with a synthetic lens implant, so the animal would remain virtually blind in any event, and also due to the relatively high cost of such veterinary procedures.

Accordingly, a method by which cataracts could be treated, in both humans and animals, by a non-surgical process would be a useful addition to ophthalmic medicine. Yet, despite much study of the cause and treatment of cataracts, a clinically useful, non-surgical treatment that retards the development of senile cataracts has thus far eluded researchers.

It is therefore the principal object of this invention to provide a clinically useful, non-surgical treatment, having virtually no side effects or complications, to reduce the symptoms, or to prevent the development, of senile cataracts in the lens of the eye of a human or animal.

It is another object of the present invention to provide a clinically useful, non-surgical treatment that will significantly retard the rate of development of senile cataracts, and thereby eliminate the need for many surgical cataract extractions.

It is yet another object of the present invention to provide a plant medicament having prophylactic and/or therapeutic properties with respect to the formation and/or progression of senile cataracts in the lens of the eye of a human or an animal.

SUMMARY OF THE INVENTION

The present invention resides in the surprising discovery, determined through preliminary in-vivo experiments described hereinafter, that the use of an extract of *Capraria biflora* effectively reduces or eliminates the lens opacity that typifies senile cataracts. It has also been found that the continued use of *Capraria biflora* effectively prevents the recurrence of senile cataracts in previously affected eyes, and also prevents the occurrence of senile cataracts in eyes at risk for developing such a condition. Methods of treating senile cataracts are provided, the methods employing an aqueous extract of *Capraria biflora* to treat a patient in need of treatment for senile cataracts. An ophthalmically stable aqueous solution appropriate for dispensing to the eye, for the prevention and/or treatment of senile cataracts, is also provided.

The aqueous solution of the invention includes an extract of *Capraria biflora* in a therapeutically sufficient amount over time so as to prevent or retard the development of a cataract in a human or animal subject to which the composition is administered. The composition may be a topical preparation or other dosage unit form suitable for instillation in the human or animal eye topically, systemically, or intraocularly. Topical dosage forms may include liquid eye drop preparations or ointments that may be instilled externally to the eye, or adsorbed into a material such as a soft contact lens or a collagen corneal shield. On the other hand, intraocular administration may take such forms as periocular injection or intraocular instillation (for example, by implantation of an intraocular reservoir).

The methods of the invention include methods for inhibiting or preventing the development of a senile cataract, or for inhibiting the progression of an incipient senile cataract, in a human or animal subject, which methods comprise administering to such a human or animal subject an aqueous extract of *Capraria biflora* in a therapeutically sufficient amount to prevent or retard the development of a senile cataract in such a subject.

In one embodiment of the invention, an extract of *Capraria biflora* is applied to the affected eye which treats an existing senile cataract. In another embodiment, the continued use of such an extract effectively prevents a senile cataract from recurring in the affected eye. In yet another embodiment of the invention, such an extract is used as a prophylactic treatment to reduce the risk of developing a senile cataract.

In a further embodiment of the invention, such an extract is used in conjunction with ocular surgery, e.g., a patient with a severe senile cataract may first be treated with such an extract to diminish the severity of the cataract, which is subsequently removed using conventional ocular surgical techniques. In yet another embodiment of the invention, such an extract may be used post-operatively.

These and other objects, aspects, features and advantages of the present invention will become more apparent from, and will be understood more clearly by reference to, the following detailed description of the presently most preferred embodiment thereof.

DETAILED DESCRIPTION OF THE PREFERRED EMBODIMENT

The preferred and other embodiments of the present invention will now be further described. Although the invention will be illustratively described hereinafter with reference to an herbal nutraceutical formulation comprising an aqueous extract of a particular plant species, it should be understood that the invention is not limited to aqueous extracts, but extends to formulations (and to methods utilizing them) that are prepared using other available extraction techniques, provided that each one yields the active components which are present in the plant species and that exhibit the salutary bio-efficacious properties of the present invention as disclosed herein.

The present invention resides in the surprising finding that an extract of the plant *Capraria biflora* can be formulated into compositions that are useful for preventing the formation of senile cataracts, or for treating such cataracts, especially by slowing their progression, in animals, including humans. *Capraria biflora* is an evergreen shrub that ranges from the southern United States though Central America and the Carribean to Bolivia in South America. The plant, the formal name of which is *Capraria biflora* L., is a member of the Family Scrophulariaceae, and is also known variously as *Capraria lanceolata*, goat weed, wild tea, savadilla, té del pais, thé du pay, ditay paye and balsaminha. Indigenous groups in South and Central America have used the leaves of *Capraria biflora* as an analgesic, anti-inflammatory, anti-pyretic, anti-arthritic, as well as for relief of gastrointestinal disturbances, to treat hemorrhoids and to treat ophthalmia (inflammation of the eye). However, prior to the development of the present invention, no use of any of the tissues of *Capraria biflora*, or of any extract thereof, to reduce or eliminate the lens opacity that typifies any type of cataract, has ever been recorded.

A naphthoquinone compound (6,9-dimethyl-3-(4-methyl-3-pentenyl)naphtho[1,8-bc]-pyran-7,8-dione), designated biflorin, has been isolated from the leaves and roots of *Capraria biflora*, and this compound has been shown to have some antimicrobial and cytotoxic activity against tumor cells. Other compounds which have been isolated from the leaves of *C. biflora* include 2,4a,5,8a-tetramethyl-1,2,3,4,4a,7,8,8a-octahydronaphthalen-1-ol, and 2-isopripyl-5,5-dimethylcyclohex-2-enone. However, research conducted thus far has not revealed whether any of the specific compounds mentioned in this paragraph is responsible for, contributes to, or even plays some role in, the bio-efficacious activity exhibited by the invention as disclosed herein.

In a preliminary in-vivo experiment conducted by applicant, which will be described in further detail hereinafter, it was discovered that an extract of *Capraria biflora* was useful in ameliorating the effects of cataracts in an animal, specifically, a canine. It was initially thought that such an extract would be useful in preventing and/or treating all classes of cataracts, in humans as well as in other animals, but further in-vivo experiments with rats, in which diabetic cataracts had been induced, showed that such extracts were not useful in preventing and/or treating the diabetic cataracts in such rats, indicating that such extracts probably would probably not be useful in treating diabetic cataracts in other mammals either. Still later in-vivo experiments with human patients, also to be described below, showed that such extracts were useful in preventing and/or treating senile cataracts, from which the canine patient had undoubtedly suffered as well. Thus, while at present this invention finds use in the prevention and/or treatment of senile cataracts, further research may reveal that such extracts may be useful in treating non-senile, non-diabetic cataracts, such as steroid-induced cataracts or cataracts induced by exposure to chemicals or to radiation.

In a preferred embodiment of the invention, an extract is prepared from the leaves of *Capraria biflora*, as described in further detail below. The extract may be prepared from such leaves in intact form, or the leaves may first be ground or otherwise processed to maximize the efficiency of the extraction process. In alternative embodiments, other parts of the *Capraria biflora* plant, including its flowers, roots, stems, stalks, twigs and/or seeds, may be used in preparing the extract, as it is believed that whatever the active components may be, which are present in the leaves of the plant and which exhibit the salutary properties of the present invention, may be found in the other other vegetative and reproductive organs of the plant as well.

In one embodiment of the invention, the extract is prepared by a conventional aqueous extraction method, that is, by mixing the leaves of *Capraria biflora* with hot or boiling water. Specifically, the aqueous solution is prepared as follows: eight (8) leaves of *C. biflora* are cut into small pieces and are placed into a 3-ounce cup, and a balanced salt (aqueous sodium chloride) solution, having a temperature in the range of 70° C.-120° C., is poured over them. Benzalkonium chloride (also known as alkyldimethylbenzylammonium chloride) is then added as a preservative, and the solution is allowed to stand for two (2) days in a refrigerator. The leaves are then removed, and the remaining liquid, constituting the aqueous extract, may then be used in accordance with the invention, although it is expected that the aqueous extract will have maximum potency immediately after its preparation, and that the effectiveness of the aqueous extract will diminish over time. If the aqueous extract is to be used directly, for topical instillation into the eye in liquid form, that is, as eye drops, then the extract solution should be shaken prior to use.

Although as set forth above the leaves may be mixed with the water directly, they may alternatively first be placed in a water-permeable bag, so as to facilitate removal of the spent leaves from the extract solution thereafter.

In other embodiments of the invention, the aqueous extract may be concentrated by conventional methods before further use is made of it in accordance with the invention. In still other embodiments, *Capraria biflora* or its aqueous extract is extracted with an organic solvent to further separate the active components from non-active components. Such solvents may include alcohols such as methanol, ethanol or isopropanol, ketones such as acetone or methyl-ethyl ketone, esters such as ethyl acetate or butyl acetate, halogenated solvents such as methylene chloride or chloroform or hydrocarbon solvents such as hexane or toluene. In yet other embodiments, the individual components of the extract may be isolated using conventional chromatographic techniques upon conventional supports such as silica, alumina, size-exclusion and ion-exchange resins. In further embodiments, the individual components of the extract may be separated using distillation, crystallization and/or chemical derivatization. Such techniques are well known to those having skill in the chemical arts.

The nutraceutical compositions of the present invention can be formulated for prophylactic and/or therapeutic administration by various methods that are well known in the ophthalmic arts, maintaining required sterility and osmolarity. For example, in another embodiment, the aqueous extract, its concentrate or purified components thereof may be mixed with conventional pharmaceutically acceptable excipients designed to increase the stability of the extract, or of its concentrate or its purified components, so as to facilitate application to the eye, or to prolong the residence of the extract, its concentrate or its purified components upon the ocular surface. Such excipients are well known to those having skill in the ophthalmic arts. The extract, its concentrate or its purified components may be applied in conventional pharmaceutically acceptable vehicles such as a solution.

As indicated above, topical instillation in the eye is the preferred method of administration, most preferably in the form of liquid eye drops, although in addition to the alternative embodiment mentioned above of being administered topically combined with an ophthalmic ointment or lubricant, the aqueous extract, its concentrate or purified components thereof can also alternatively be administered by being adsorbed into a soft contact lens (e.g., that marketed by Johnson & Johnson under the trade name "Accuvue Advance") or a dissolvable collagen corneal shield.

The nutracuetical compositions of the present invention can alternatively be administered either systemically or by intraocular means, although at present these administration routes are less preferred. Regarding systemic administration, that is, oral or parenteral administration, the aqueous extract, its concentrate or purified components thereof may be incorporated into tablets, pills, capsules, etc., wherein the extract, its concentrate or purified components thereof is/are dispersed in one or more pharmaceutically acceptable, preferably biodegradable, carriers, and wherein the delivery system may also include one or more of the following: binders, excipients, lubricants, glidants and/or sweetening agents.

Regarding intraocular administration, that is, direct infusion into the eyeball, the aqueous extract, its concentrate or purified components thereof can be administered via injection, or by other delivery routes known in the ophthalmic arts that are applicable to administer a drug to the eye. These administration routes can be advantageous when direct treatment of the ocular lens, or the provision of a continuous supply of the aqueous extract, its concentrate or purified components thereof to the eye may be required. However, as it is expected that discontinuous treatment over time will be the most effective form of therapy, and since, at least for human patients, a non-invasive administration method that also admits of self-administration may be preferable, preparations which can be administered topically, particularly as liquid eye drops using a conventional eye dropper, are most preferred.

When administered in that form, as a non-concentrated aqueous extract of *Capraria biflora* which has not been further purified or further extracted with any organic solvents, the preferred dosage is one drop (equivalent to 50 µl) in each affected eye, three times per day, over the course of four to six weeks. It has been found that for such a dosage regimen, the aqueous extract should be replaced with a freshly-prepared aliquot at least once every two weeks, and that any remaining unused extract in the previous aliquot should not be used. It is also preferable that each aliquot of the aqueous extract be kept refrigerated when not in use.

The following working examples illustrate both the manner in which such an aqueous extract of *Capraria biflora* in accordance with the present invention has been used in both human and animal subjects suffering from at least one senile cataract, and the experimental results obtained, which demonstrate the efficacy of the invention.

Example 1

An elderly male animal, specifically a canine of the dachshund breed, aged 16 years, was observed as having chronically irritated, red eyes which made him visibly uncomfortable, and also as having greatly impaired vision due to cataracts. The impairment of his vision was deduced empirically from his behavior: the subject was observed bumping into walls and being unable to find his toys, as well as being unable to find his food, except by using his sense of smell. An ophthalmologic examination of the animal confirmed the presence of very dense cataracts in both eyes.

An aqueous extract of *C. biflora* was prepared and was placed in an eye dropper; this extract was prepared in accordance with the invention, except that only five leaves of *C. biflora* were used, no preservative was added, and instead of cooling the extract by refrigeration, it was allowed to stand at room temperature until it cooled.

One drop was administered to each eye of the canine subject, three times per day, for about one week at a time, which resulted in a reduction in the observed eye redness and eye irritation, as well as an increase in the subject's comfort with his eyes. The administration of the extract was interrupted on several occasions, upon which the irritation in the subject's eyes returned within one or two days, but when the administration of the extract was thereafter resumed, the irritation was observed to decrease once again.

After administration of the extract continued without interruption for three weeks, it was observed that the canine subject's vision had improved as well. This was deduced empirically from the animal's behavior: he ceased bumping into walls, found his toys and his food more easily, and could navigate generally without any observed visual impairment, from which it was concluded that the administration of the extract had reduced the cataracts from which the animal had suffered.

Example 2

A 78-year old Caucasian female with a 20/60 senile cataract in the right eye and a 20/30 senile cataract in the left eye underwent a full ophthalmological examination, which revealed no pathology in either eye except for the cataracts. A picture was taken of the right eye at this time.

An aqueous extract of *C. biflora* was prepared in accordance with the invention, was placed in an eye dropper, and was given to the patient, who thereafter self-administered one drop three times a day, seven days a week, for three weeks, without missing a single dose, but only in the right eye. The patient was given, and thereafter used, a freshly-prepared aliquot of the aqueous extract once per week, and each aliquot was kept refrigerated when not in use.

Another ophthalmological examination was conducted three weeks after the first administration of the extract. The vision in the right eye had improved to 20/30, and upon visual inspection the cataract appeared noticeably clearer. The remainder of the ophthalmological examination was within normal limits. Another picture of the cataract in the right eye was taken at this time for purposes of comparison.

The patient reported that she "could see again" and could perform all of her normal daily activities. Administration of the extract was therefore discontinued.

Example 3

An 81-year old Caucasian female, who had 20/60-vision in both eyes due to senile cataracts, underwent a full ophthalmological examination and no pathology was found in either eye except for the cataracts. Pictures were taken of both cataracts at this time.

An aqueous extract of *C. biflora* was prepared in accordance with the invention, was placed in an eye dropper, and was given to the patient, who thereafter self-administered one drop in each eye three times a day, seven days a week, for four weeks, without missing a single dose. The patient was given, and thereafter used, a freshly-prepared aliquot of the aqueous extract once per week, and each aliquot was kept refrigerated when not in use.

Another ophthalmological examination was conducted four weeks after the first administration of the extract. The vision in the both eyes had improved to 20/30, and upon visual inspection the cataracts appeared noticeably clearer. The remainder of the ophthalmological examination was within normal limits.

The patient reported that she could now read the newspaper again, something she hadn't been able to do for five years.

Based on the experimental results summarized above, it is believed that the present invention comprises treatment methods and compositions that can ameliorate the effects, and/or inhibit the development, of senile cataracts in an animal subject, for example, a dog, a cat, a horse, a cow, a mouse, a rat or a human. As to human subjects in particular, it should be understood that, when used propylactically, although any patient in a demographic group at significant risk for senile cataracts can be treated (for example, humans over the age of 50), subjects can also be selected using more specific criteria. For example, patients who have biomicroscopic clinical evidence of an incipient senile cataract, or patients who have biomicroscopic evidence of a senile cataract combined with a decrease in visual acuity, can be selected for treatment.

The present invention is useful in the treatment and/or prophylaxis of senile cataracts, and therefore finds industrial applicability in human and veterinary medicine.

While there has been described what are at present considered to be the preferred embodiments of the present invention, it will be apparent to those skilled in the art that the embodiments described herein are by way of illustration and not of limitation. Therefore, it is to be understood that various changes and modifications may be made in the embodiments disclosed herein without departing from the true spirit and scope of the present invention, as set forth in the appended claims.

The invention claimed is:

1. A method of treating a senile cataract in a human or veterinary patient, comprising administering a therapeutically effective amount of an extract of *Capraria biflora* to a human or veterinary patient in need of such treatment.

2. A method in accordance with claim 1 wherein said extract is an aqueous extract and is prepared from at least one organ of said Capraria biflora selected from the group consisting of leaves, stems, stalks, twigs, flowers, roots, and seeds.

3. A method in accordance with claim 2 wherein said extract is prepared from the leaves of *Capraria biflora*.

4. A method in accordance with claim 1 wherein said extract is administered topically, systemically or intraocularly.

5. A method in accordance with claim 4 wherein said extract is administered topically to an afflicted eye of the patient in the form of liquid eye drops.

6. A method in accordance with claim 5 wherein said patient is human and said extract is administered in an amount comprising substantially 0.15 ml daily, for a period of four to six weeks.

7. A method in accordance with claim 6 wherein said extract is an aqueous extract prepared from at least one organ of said Capraria biflora selected from the group consisting of leaves, stems, stalks, twigs, flowers, roots, and seeds.

8. A method in accordance with claim 7 wherein said extract is administered together with one or more pharmaceutically acceptable excipients and/or carriers.

9. A non-surgical method of alleviating a senile cataract in the eye of a, human or animal subject comprising the step of administering an herbal medicament to alleviate the senile cataract in the eye of a human or animal subject, the medicament comprising a therapeutically effective amount of an extract of *Capraria biflora* prepared from at least one organ of said *Capraria biflora* selected from the group consisting of leaves, stems, stalks, twigs, flowers, roots, and seeds.

10. A method in accordance with claim 9 wherein said extract is an aqueous extract and is prepared from the leaves of *Capraria biflora*.

11. A method in accordance with claim 10 wherein said subject is human.

12. A method in accordance with claim 9 wherein said extract is administered topically, systemically or intraocularly.

13. A method in accordance with claim 12 wherein said extract is administered topically to an afflicted eye of the subject in the form of liquid eye drops.

14. A method in accordance with claim 13 wherein said subject is a human being and said extract is administered in an amount comprising substantially 0.15 ml daily, for a period of four to six weeks.

15. A method in accordance with claim 14 wherein said extract is an aqueous extract prepared from the leaves of *Capraria biflora*.

16. A method of treating a senile cataract in a human or animal patient in need thereof comprising the step of administering to said human or animal patient a therapeutically effective amount of a composition comprising an extract obtained from *Capraria biflora* and one or more physiologically acceptable additives.

* * * * *